United States Patent [19]

Nichols

[11] 4,029,726

[45] * June 14, 1977

[54] CELLULOSIC-LIQUID COMPOSITE MATERIALS AND PROCESS OF PREPARING SUCH MATERIALS

[75] Inventor: Larry D. Nichols, Arlington, Mass.

[73] Assignee: Moleculon Research Corporation, Cambridge, Mass.

[ * ] Notice: The portion of the term of this patent subsequent to Nov. 5, 1997, has been disclaimed.

[22] Filed: Oct. 29, 1974

[21] Appl. No.: 518,797

Related U.S. Application Data

[63] Continuation-in-part of Ser. No. 363,267, May 23, 1973, Pat. No. 3,846,404.

[52] U.S. Cl. .................................. 264/41; 106/178; 106/187; 106/188; 106/189; 106/190; 106/195; 106/196; 210/500 M; 264/342 R; 427/246; 427/339

[51] Int. Cl.² .................. B29D 27/04; B29H 7/20; C08L 1/12

[58] Field of Search .......... 106/189, 190, 195, 197, 106/196; 260/13, 223, 220; 264/41, 49, 212; 210/23 H, 321 R, 400, 491, 500 N

[56] References Cited

UNITED STATES PATENTS

| | | | |
|---|---|---|---|
| 2,843,582 | 7/1958 | Voris | 260/223 |
| 3,341,515 | 9/1967 | Connelly | 260/223 |
| 3,520,960 | 7/1970 | Douglas | 264/49 |
| 3,580,841 | 5/1971 | Cadotte et al. | 210/23 H |
| 3,775,308 | 11/1973 | Yasuda | 210/23 H |
| 3,846,404 | 11/1974 | Nichols | 264/41 X |

OTHER PUBLICATIONS

Pierce, H.F. Nitrocellulose Membranes of Graded Permeability, In J. Brot Chemistry, 75, pp. 795–815, 1927.
Riley, R. L. et al. "Improved Reverse Osmosis Membranes," U.S. Department of Interior, Office of Saline Water Research and Development Progress Report No. 729, Dec. 1971. TD433 U56 No. 729 pp. 1–14, 101–112.

Primary Examiner—J. Ziegler
Attorney, Agent, or Firm—Richard P. Crowley

[57] ABSTRACT

Polymer-liquid composite materials, particularly of cellulosic polymers such as cellulose nitrate, are described, which materials are strong, transparent, ultramicroporous materials characterized by a diffusion-supporting liquid phase of about 70% or more liquid within an interpenetrating, form-retentive, solid polymer phase. The materials are prepared by precipitation from a hydrogen-bonding solvent solution by the use of a miscible nonsolvent at temperatures generally below about 45° C.

15 Claims, No Drawings

CELLULOSIC-LIQUID COMPOSITE MATERIALS AND PROCESS OF PREPARING SUCH MATERIALS

REFERENCE TO PRIOR APPLICATION

This application is a continuation-in-part of my copending application Ser. No. 363,267, filed May 23, 1973 (now U.S. Pat. No. 3,846,404, issued Nov. 5, 1974), the disclosure of which is hereby incorporated by reference in this application.

BACKGROUND OF THE INVENTION

The products of this invention are materials containing distinct, interpenetrating polymer and liquid phases of submicroscopic, but supramolecular, dimensions. Such products are referred to as a polymer-liquid composite (PLC).

A PLC material can serve as media for diffusive and permeative phenomena commonly associated with pure liquids, while displaying the physical form and integrity of solids, and is useful for controlling the release or exchange of liquids and solutes, while their finite internal pore size allows processing and partitioning of liquids and solutes on the basis of molecular size and shape. Further, a PLC can be used in many applications where some known liquid possesses desirable chemical, electrical or other properties, but lacks the required mechanical integrity. These useful properties often are enhanced at high liquid-to-solid ratios. The present invention presents a unique, novel and general category of high liquid content PLC material which, unlike familiar high liquid content polymer gels, retains good mechanical properties.

The PLC materials of this invention are distinct from the plasticized polymers of commerce, such as polyvinylchloride/dioctyl phthalate and polymeric gels, such as gelatin or cross-linked polyacrylamide. Plasticized polymers, even when their liquid content reaches or exceeds 50%, can be considered rather accurately as solutions of a liquid in a solid. The physical properties of plasticized polymers can be and generally are profoundly modified by the presence of the liquid; tensile strength and elastic moduli are reduced, and softening points or transition temperatures fall to lower values than those for the pure resin, and such changes are often of crucial commercial importance. Such common plasticized polymers are categorized as rather soft and elastic solids. Liquid transport through such materials, even at high pressure gradients, is too slow to be useful for membrane separation processes and the rapid diffusion characteristic of the free molecular motion found in pure liquids is not exhibited by plasticized polymers. The dispersion of the polymer and liquid phases in plasticized resins is essentially molecular, and encounters between moving fluids or individual molecules and the immobile polymer molecules are extremely frequent, leading to virtual immobilization of the entire system.

At much higher liquid concentrations, I find the common polymer gels, which may shown some nonamorphous morphology, particularly when based on proteins or polysaccharides with their stereospecific biological origin and strong hydrogen-bonding ability. Nevertheless, the degree of dispersion of the polymer and liquid in each other is still generally molecular, with the solid or semisolid characterisctics of the gel arising from entanglement or weak bonding between the long, intermingled polymer chains. Synthetic gel-forming polymers, such as polyacrylamide, are often cross-linked to impede further relative motion and enhance physical integrity. Fluid and diffusive mobilities within such gels can be high when there is very little polymer present, but this low polymer concentration and the lack of any pronounced morphological reinforcement between neighboring molecules leads to very low physical strength, often defeating the very application for which the gel would otherwise be suited. For example, one gains little through preparing a gel which would give rapid liquid flux rates through a thin film at some given pressure gradient, if the gel itself collapses under the applied pressure.

These two classes of materials, plasticized polymer and polymer-liquid gels, have in common the feature that, although composed of two distinguishable substances, one a liquid and the other a solid, on any scale of much more than molecular dimensions, they present all of the characteristics of a single phase material, and are not considered to be true composites. Just as some metals alloy randomly in all proportions, while others precipitate as separate phases to produce materials such as steel or alnico with a whole new set of properties, so liquids and polymers can in some cases function merely as mutual solvents and solutes, or alternatively separate into distinct interpenetrating phases and develop characteristics found in neither alone. It is this latter category which is termed polymer-liquid composites (PLC), and which comprises the materials of the invention.

SUMMARY OF THE INVENTION

My invention comprises a novel and unique family of strong, transparent, ultramicroporous polymer-liquid composite materials possessing a mobile and diffusion-supporting liquid phase within an interpenetrating, form-retentive solid phase, and methods for the preparation and use of such materials. In particular, my invention relates to polymer-liquid composite material (PLC) in which the polymer is an electronegatively substituted cellulose derivative precipitated from a hydrogen-bonding solvent by displacement of that solvent by a miscible nonsolvent at non-elevated temperatures. The products of my invention shown in addition to the above-mentioned properties the ability to exchange freely their liquid component for another, miscible liquid non-solvent by simple immersion, and resistance to imbibation of additional liquid even after complete or partial removal of the original liquid content, and are strong, flexible, transparent and isotropic.

There are a number of characteristics which distinguish my PLC material from other kinds of materials which also contain both liquids and polymers. The presence of interconnected crystalline aggregates in the PLC of dimensions much larger than those of an individual molecule leads to enhanced strength and rigidity, and stabilizes the PLC material against engorgement of additional liquid, since this would require the destruction or disaggregation of portions of the solid structural elements to allow development of a larger, more diffuse network. Removal of liquid is possible, since there is little to prevent further coalescence of neighboring aggregates, but such removal is irreversible. Exactly this behavior is shown by the PLC material of this invention, whereas gels and plasticized resins typically swell readily in the presence of excess liquid, unless cross-linked, in which case swelling is impeded.

A second characteristic of the PLC microaggregate structure results from the presence of supramolecular solid aggregates associated with purely liquid-filled regions with dimensions far exceeding those of individual molecules. The existence of such a submicroscopic, but supramolecular, continuous liquid phase allows liquid transport phenomena at practical pressure gradients of a few tens of psi per mil according to well-known Kozeny equation for fluid flow through porous media. Finally, the supramolecular liquid phase supports diffusive phenomena almost as well as the pure liquid, for solute mean-free paths in a liquid are on the order of intermolecular distances, and far shorter than the wall-to-wall distances of the PLC liquid-filled pores. In PLC materials, observed diffusion rates, after correction for the volume of space actually occupied by water in the PLC, prove to be almost identical with those for pure water.

To prepare PLC material containing a high ratio of liquid-to-solid without excessive sacrifice of strength, the solid phase must be continuous or composed of discrete regions so large and complex as to resist relative motion. Mechanical mixing cannot alone produce such a macroscopic solid phase, which must be formed and grown directly within a liquid medium. The process requires initial solution of the polymer in some solvent, followed by a reduction in solvent power to initiate and continue precipitation of the polymer in an aggregated, microporous form. As in all chemical precipitations, the morphology of the produced solid phase can vary widely with the precipitation conditions. The long polymer chains favor the formation of an interconnected solid network, but the size and degree of packing of the interconnected solid elements within the residual liquid depends on such factors as the length and rigidity of the polymer molecules, the strength of chain-chain forces, the strength of chain-liquid forces, and steric factors governing the ability of liquid molecules to pack tightly around the chains and inhibit coalescence into a dense, liquid-free form during the early, fragile stages of precipitation and network formation.

Optimum conditions for formation of strong, high liquid content PLC material include: selection of a strong, rigid, high molecular weight polymer; selection of a solvent functionally and sterically capable of strong bonding to the polymer chain; and selection of a method for reducing solvent power at temperatures low enough to avoid thermal sintering or coalescence of the precipitate.

These criteria are met in particular by cellulosic polymers, strong polar solvents, and precipitation by rapid displacement of the solvent by a miscible nonsolvent. It has been discovered that homogeneous, ultramicroporous PLC material can be prepared by such criteria. Certain further requirements have been discovered to be essential; namely, the cellulose chain must have its free hydroxyls largely replaced by small electronegative groups; the solvent must be capable of hydrogen-bond donation; the nonsolvent must be freely miscible with the solvent; and the solvent displacement operation must be conducted below or only slightly above room temperature; e.g., less than about 45° C, such as below 30° C. Departure from these requirements leads to precipitated materials which either contain relatively little liquid content, or are macroporous and physically weak. Such weak, hazy products represent a transition case between the desired strong, ultramicroporous products and the discrete, powdery precipitates often obtained when polymer solutions are mixed with nonsolvents. Compliance with the above criteria leads to transparent, homogeneous, ultramicroporous PLC material containing about 70 to 99+% liquid, while retaining good physical properties.

The PLC materials of my invention are prepared from a solution of an electronegatively substituted cellulose derivative; for example, such as 0.5 to 15% by weight of the polymer, such as cellulose nitrate, in a nondegrading hydrogen-bonding solvent, such as acetic acid, by forming said solution into a desired shape and precipitating the product with a miscible nonsolvent, such as water, at a temperature below 45° C; e.g., 35° C; i.e., 10° to 25° C. A degree of substitution of the cellulose nitrate of more than 70% is beneficial. For such cellulose nitrate, suitable combinations of solvent and coagulant include, but are not limited to: acetic acid/water; acetic acid/isopropanol; acetic acid/methylene chloride; methanol/water; methanol/isopropanol; 3:1 diethyl ether: ethanol/isopropanol; 1:4 acetone:formic acid/isopropanol; 1:2:2 acetone:acetic acid:formic acid/water; and acetic acid/glycerin. One preferred combination as a coagulating nonsolvent is water or an organic alcohol, and wherein the temperature of the coagulating contact operation is below 40° C, with the solvent being a hydroxyl- or carboxyl-containing organic liquid freely miscible with the water or alcohol, and capable of dissolving the cellulosic polymer.

The polymer content of these PLC materials can be controlled by varying the concentration of resin in the original solution, this concentration typically doubling during coagulation with water and remaining more nearly constant during coagulation with isopropanol. Other suitable electronegatively substituted cellulose derivatives include cellulose triacetates and, marginally, cellulose tripropionate. Each such alternative resin requires an optimum choice of solvent and coagulant; for mixed triacetatenitrates 1:2:2 acetone: formic acid:acetic acid is required for good initial solution, whereas acetic acid itself suffices for the tripropionate, which must be precipitated with methanol or isopropanol to avoid severe hazing and even then shows a faint haze. The cellulosic polymer may be an inorganic or organic ester of cellulose; however, the preferred cellulosic materials of my invention may include, but are not limited to: cellulose nitrate with a degree of substitution of greater than 2.25; cellulose acetate with a degree of substitution greater than 2.90; a mixed cellulose acetate-cellulose nitrate with a degree of substitution above 2.25, or a mixture of such cellulose acetates, nitrates and acetate-nitrates. Cellulose tripropionate with a degree of substitution of greater than 2.90 is acceptable. X-ray diffraction studies show that the PLC material of my invention has a crystalline structure in the polymer phase.

The PLC materials of my invention freely exchange their liquid content for any miscible nonsolvent, and shown hysteresis during evaporative liquid removal and subsequent reimmersion, no more than half the lost liquid being regained, and exhibit flux rates toward pressurized water in excess of 0.01 ml/cm$^2$/min for a 4-mil film at 30 psi, and these flux rates scale linearly with pressure and inversely with film thickness up to 20 ml/cm$^2$/min.

Complete evaporative drying of my PLC materials produces transparent, water-free materials whose density and essential physical properties resemble some of those properties of the corresponding pure resin prepared in other ways; for example, by casting from a volatile solvent. The tensile strength of cellulose triacetate generally ranges from 9000 to 16000 psi; however, the cellulose triacetate PLC materials of my invention derived from 70, 85 and 92% water as the nonsolvent have tensile strengths of 2570, 1590 and 530 psi, respectively. This drying process is accompanied by the theoretical decrease in volume, films and fibers distributing this shrinkage nonuniformly between their different summetry directions.

I have found that various grades of cellulose nitrate, differing in viscosity and molecular weight, can be successfully employed in the preparation of my PLC materials. The resulting products show few differences other than those associated with changes in processing caused by the differences in viscosity. Hydraulic flux through films of uniform thickness at a fixed applied pressure shows a tendency to decrease linearly with the log of the polymer viscosity index.

My PLC materials freely exchange solutes as well as liquid with their external environment, except in those cases where the solute in question happens to be strongly adsorbed by the internal surface of the polymer phase in the PLC material.

The PLC materials of my invention can readily be formed in a variety of shapes, including films, fibers, hollow fibers and small discrete particles, such as microspheres. The first three of these forms can be prepared by coating, casting or extruding the polymer solution directly, or after a brief interval, into a suitable coagulant or precipitating nonsolvent. Microspherical products in the size range from 1 to 500; e.g., 5 to 300, microns can be prepared by emulsification of the polymer solution in an immiscible nonsolvent, followed by coagulation of the suspension using a liquid which: (a) does not dissolve the polymer; (b) is miscible with the polymer solvent; and (c) is also miscible with the liquid used as the suspension medium. Alternatively, microspheres can be prepared by spraying the polymer solution into a coagulating liquid.

My PLC materials may optionally be contacted, such as by immersion, with a sequence of one or more sequentially miscible distinct liquid nonsolvents with or without contained solutes so as to achieve by repeated liquid-phase interchange a final polymer-liquid composite product composed of the original cellulosic polymer, a final liquid phase of choice, such as an essential oil, sweetening solutions, hydrocarbons like insulating oils, absorbent liquids, etc. and any desired solutes. For example, the sequential exchange may be water-alcohol-hydrocarbon, such as benzene, or benzene-hydrocarbon-oil, or water-alcohol-essential oil.

The liquid phase of my PLC materials may comprise a wide variety of nonsolvent liquids to include, but not be limited to: liquid monomers for later reaction or polymerization; liquid polymers; hydrocarbons; plasticizers; ethers; triglycerides; alcohols; high dielectric liquids; essential oil; insulating liquids like Nujol; polybutene, etc.

Applications for my PLC products include, but are not limited to; shrinkable packaging materials; electrical insulating and dielectric materials; media for electrophoresis, column and steric exclusion chromatography; media for radioimmunoassays; controlled release agents for fragrances, flavors, medications, cosmetic and dermitological agents; selective sorbents for organic solutes; media for dialysis, ultrafiltration and other separative operations; and as electrically and ionically conductive separators in batteries and electrochemical cells.

The new and unique polymer-liquid composite materials of my invention, their method of preparation and some uses of such materials will be described for the purposes of illustration only in connection with the following examples.

DESCRIPTION OF THE EMBODIMENTS

EXAMPLE 1

Hercules RS-60 grade cellulose nitrate (CN) was dissolved in glacial acetic acid. Solutions containing 4 to 15% CN possessed sufficient viscosity to allow film-forming operations by conventional blade-coating techniques. When such wet films, for example, with a thickness of 1 to 20 mils, were immersed in water at a temperature below 45° C, they congealed to transparent, nonhazy PLC films containing about twice as much CN by weight as the original solution. Those films with the lowest liquid content (70%) were significantly stronger than those with the highest (92%), but all were self-supporting and readily handled. Pressurized water passed through such films at a flux rate proportional to the applied pressure divided by the film thickness for any given film composition, demonstrating the homogeneous porosity of the materials; that is, the absence of any appreciable skin with a less open structure. At any given thickness and pressure, the flux rate increased more than linearly with the liquid content of the film, indicating that pore size, as well as pore volume, increases as the polymer content is reduced. These RS-60 CN products are typical of the unique family of desirable new polymer-liquid compositions constituting the invention.

EXAMPLE 2

When the RS-60 CN solutions in acetic acid described in Example 1 were congealed in water at a temperature above about 45° C, they produced films with a pronounced and readily visible haze, and were perceptibly weaker than the films of Example 1. Flux rates for pressurized water through such hazy films were higher than those for otherwise identical clear films formed at lower temperatures, indicating a larger pore size.

EXAMPLE 3

RS-60 CN is insoluble in simple carboxylic acids other than acetic acid, and in such substituted carboxylic acids as dichloroacetic, trifluoroacetic and lactic acids. Of the alcohols, only dry methanol is a solvent, although ethanol and meta-cresol swell the polymer. Use of methanol as an alternative hydrogen-bonding solvent to the acetic acid of Example 1 gives transparent, microporous PLC materials whose compositions are similar to those of Example 1 and whose flux rate toward pressurized water suggests a somewhat finer pore size.

EXAMPLE 4

There are many nonhydrogen-bond-donating solvents for RS-60 CN, including acetone, esters, tetrahydrofuran, nitromethane and dimethylsulfoxide. When these materials are used instead of acetic acid under the conditions of Example 1, the results depend on the degree of miscibility of the solvent with water, but in no case produce strong, transparent products. With water-immiscible esters, coagulation does not occur, while with marginally miscible nitromethane, a transparent precipitate of very low water content is produced. All of the other solvents listed are readily miscible with water, and all give weak, hazy products with extremely high flux rates toward pressurized water.

EXAMPLE 5

Although neither diethyl ether nor ethanol is a solvent for RS-60 CN, a 3:1 ether-alcohol mixture constitutes the wellknown collodion solvent system for cellulose nitrates. This mixed solvent possesses some hydrogen-bond-donating power by virtue of its alcohol content, but such solutions cannot be processed as in Example 1 because of the insolubility of ether in water. Coagulation with pure ethanol gives only a soft, gelatinous material impossible to handle. Coagulation with isopropanol proceeds in a manner entirely analogous to that of Example 1, giving strong, clear films of normal composition.

EXAMPLE 6

The experiment of Example 5 differs from that of Example 1 not only in the solvent used, but in the use of an alcohol as the coagulant. Repetition of Example 1 using RS-60 CN in acetic acid, but replacing the water with isopropanol, leads to strong, transparent microporous products whose final water content after replacement of the isopropanol by water is higher than the corresponding polymer-liquid composites of Example 1, with an 8% solution leading to a final material containing about 90% water.

EXAMPLE 7

Further experiments show that other coagulants, whether or not miscible with water, can be successfully used to replace water in Example 1, so long as they are miscible with the acetic acid solvent. In these cases, it is necessary to replace the original coagulant with an intermediate liquid miscible both with it and with water before final isolation of the product as a water-containing composite. Butanol and methylene chloride are both effective as coagulants and can be displaced first with isopropanol and then with water to give products resembling those of Example 6.

EXAMPLE 8

Examples 6 and 7 involve the replacement of one liquid constituent of the polymer-liquid composite by another miscible liquid. Experiments show that this exchange occurs readily upon immersion of the composite material in the replacement liquid so long as the new liquid is also a nonsolvent for the polymer, and that the physical form and liquid-to-solid ratio of the composite suffers little or no change during such replacements. As one specific instance, a sample of composite containing 85% water as prepared according to Example 1 had its water replaced by isopropanol, the isopropanol by decalin, and the decalin by mineral oil without damage or a significant change in liquid content.

EXAMPLE 9

Although various liquid constituents of the liquid-polymer composites of this invention can be interchanged as in Example 8, the process of complete or partial removal of the liquid phase, for example, by evaporation, shows strong hysteresis and is essentially irreversible. Samples of PLC material prepared with 85% liquid content according to Example 1 showed the following behavior:

| Fraction of Water Allowed to Evaporate | Fraction of Water Regained During Immersion in water for 72 Hr. |
|---|---|
| 25% | 13% |
| 50% | 13% |
| 75% | 6% |
| 100% | 0% |

This drying process is accompanied by the expected decrease in sample volume, the final dry product having the density of pure RS-60 CN.

EXAMPLE 10

Variations in the polymer-liquid composite product due to variations in the molecular weight of the polymer were investigated using RS-grade CN samples with viscosity indexes ranging from 5.1 seconds up to 4350 seconds. The CN used in Example 1 had a viscosity index of 60 seconds. Viscosities below 16 seconds gave low viscosity solutions in acetic acid which were difficult to form into films and showed faint haziness after coagulation, while deformation of the wet film during immersion for coagulation was also difficult to avoid. The products when carefully prepared showed the normal liquid content exemplified in Example 1 for RS-60. Viscosity indexes above 1000 seconds required warming of the solution to lower its viscosity for film forming, while coagulation was still conducted at temperatures well below 25° C. Films showed some superficial roughness due to difficulties in film drawing, but only very faint haziness and gave normal liquid contents. Over the range from 20 to 1000 seconds, all RS cellulose nitrates gave good products with standard liquid contents. The flux rate toward pressurized water, corrected for film thickness, applied pressure and liquid content, showed a linear decrease with the logarithm of the viscosity index.

EXAMPLE 11

The effect of degree of substitution was investigated using CN sample of Hercules grades SS-49 and AS-5.8. SS, AS and RS grades are, respectively, about 11%, 11.5% and 12% nitrogen, corresponding to degrees of substitution of 65%, 70% and 75%. Polymer-liquid composite materials prepared from grades SS and AS according to the process of Example 1 were white and brittle, although their liquid contents corresponded to the normal values of Example 1. Like most such hazy materials, flux rates toward pressurized water were high when compared with the transparent films of my invention. CN of a degree of substitution greater than 13% can be formed into PLC material only by the use of mixed solvents, such as 2:3 acetone: formic acid, log coagulation temperatures, and particular care in the preparation of solutions.

EXAMPLE 12

While Example 4 showed that nonhydrogen-bond-donating solvents are incapable of forming strong, transparent high liquid content polymer-liquid composites, experiments have shown that moderate amounts of such solvents, like volatile ketones such as acetone, can be used in combination with one or more carboxylic acids without detriment. Such mixed solvent systems are more readily tolerated if coagulation is conducted in isopropanol rather than water. Acceptable PLC products can be obtained from the following solvent systems for RS-60 CN: 1:4 acetone:acetic acid; 1:4 acetone:formic acid; and 1:2:2 acetone:formic acid:acetic acid. The range of behavior obtainable with acetone is exemplified by its use with formic acid. With 10% or less acetone, the CN is incompletely soluble; 20% acetone gives good products, while 50% acetone leads to low water content, somewhat hazy materials. Other strong, but nonhydrogen-bonding solvents, such as tetrahydrafuran (THF), show similar behavior.

EXAMPLE 13

Examples 1-12 deal with nitrate esters of cellulose as polymers for forming strong, transparent, microporous polymer-liquid composites. The electronegativity of the nitrate groups is essential as illustrated by experiments on a variety of other much less electronegatively substitited cellulose derivatives. Specifically, the use of the process of Examples 1, 6 or 7 on highly substituted ethyl cellulose gives white, readily shredded products with low water contents.

EXAMPLE 14

Intermediate in electronegativity between nitrate esters and ethers, such as ethyl cellulose, lie the cellulose ester derivatives of the carboxylic acids. These provide an opportunity to test a range of substituents differing primarily in size. At the lower extreme lies cellulose triformate, which rapidly hydrolyzes in water, and an upper boundary is presented by cellulose tridecanoate, which is insoluble in most of the solvents found suitable for the process of my invention. It is soluble in dichloroacetic acid and gives disintegrated white waxy ppts when such solutions are coagulated with methanol or isopropanol. Intermediate in size lie the esters of acetic and propionic acid. Of these, acetate esters of cellulose are found to perform well under the conditions of Example 1 for degrees of substitution of 90% or higher. Lower degrees of substitution lead to hazy products with reduced strength and increased flux rates toward pressurized water, and even with degrees of substitution of more than 90%, some hazing can be observed if coagulation is conducted much above 30° C, a somewhat lower threshold than that for the cellulose nitrates. The need for higher degrees of substitution and lower temperatures is consistent with the lower electronegativity of the acetyl group as compared with the nitro group. Cellulose tripropionate is markedly inferior to the triacetate, forming good products only under carefully controlled conditions with isopropanol as the coagulating liquid, and even in this case, a faint persistent haze can be detected.

EXAMPLE 15

Cellulose possesses not only various pure ester and nitrate derivatives, but can be processed into mixed esters containing more than one kind of substituent within a single cellulose molecule. Cellulose acetate-propionates are markedly inferior to cellulose triacetate, and the acetate-butyrates provide only weak, white products, whereas cellulose acetate-nitrate forms good, clear, and strong PLC materials, as do mixtures of cellulose triacetate with RS-grade cellulose nitrate. The acetate-nitrates, both as heterosubstituted polymers and as mixtures of the pure polymers, are much less soluble than either the pure triacetate or the pure nitrate, and a mixed solvent, such as 1:2:2 acetone:formic acid:acetic acid, is required to process these materials. Liquid contents follow Example 1, and flux rates toward pressurized water are somewhat higher than those of the pure triacetate or pure nitrate, indicating a less ordered, more open pore structure.

EXAMPLE 16

Cellulose triacetate is soluble in many nonsolvents for cellulose nitrate, providing an opportunity to test additional solvents. The requirement for hydrogen-bond-donating ability is still substantiated. Solvents lacking this capability give only weak, white products. Examples include dimethylsulfoxide, pyridine, and chlorinated hydrocarbons. Cellulose triacetate is soluble in aromatic alcohols, such as meta-cresol, and gives good, strong, clear products when precipitated from meta-cresol with methanol or isopropanol. It is soluble in many carboxylic acids, including formic, acetic, dichloroacetic and trifluoroacetic acid. Of these, all except dichloroacetic acid give good products when coagulated with water. Dichloroacetic acid, which is marginally miscible with water but freely miscible with alcohols, gives good, nonhazy products when methanol or isopropanol are used as coagulants. As with cellulose nitrates, cellulose triacetate solutions in strongly hydrogen-bonding solvents can tolerate 10 to 20% dilution with nonhydrogen-bonding liquids, such as acetone or tetrahydrofuran, without detriment.

EXAMPLE 17

The preferred polymers of my PLC materials are cellulosic polymers. These polymers have the essential ingredient of forming strong, homogeneous, high liquid content PLC materials. The rigidity of the cellulose chain and its pronounced tendency to aline with parralel chains to form strong micellar aggregates renders it exceptionally suitable. Experiments with a wide variety of commercially important noncellulosic polymers have revealed none which produce strong, porous and transparent products upon coagulation of a polymer solution with a miscible nonsolvent. Table I shows specific polymer systems investigated without success.

TABLE I

| Noncellulosics Tested for PLC-Forming Capability | |
|---|---|
| Polymer | Observations |
| Nylon-66 | Soluble in formic acid; coagulates in water to a brittle, white film. |
| *Qiana Nylon | Soluble in formic acid; coagulates in water to a coherent white film which remains white on drying. |
| Polyacrylonitrile | Insoluble in both formic acid and meta-cresol at temperatures up to 100° C. |
| Polysulfone | Insoluble in formic acid; dissolves in hot meta cresol; a 20% solution coagulates in methanol to give a strong opaque white film which dries to a white, low-density solid. |
| Polyethylene Terephthalate | Insoluble in formic acid; soluble in hot meta cresol; coagulation with methanol gives a cloudy, semigelatinous product. |
| Polymethyl Methacrylate | Soluble in formic acid; 8% and 20% solutions can be coagulated with water or methanol to give white, coherent films which remain white on drying the low-density solids. |
| Polyvinylalcohol | Soluble in formic acid; contact with water or alcohols leads to dissoluton; coagulation with benzene gives an incoherent, gelatinous material. |
| Polyvinylacetate | Soluble in formic acid; an excessively viscous 8% solution diluted to 2% failed to coagulate in benzene or trichloroethylene; coagulation with methanol gave an |

TABLE I-continued

| Noncellulosics Tested for PLC-Forming Capability | |
|---|---|
| Polymer | Observations |
| | incoherent gelatinous material showing pronounced haziness. |
| **Lexan Polycarbonate | Insoluble in formic acid; soluble in hot meta cresol; coagulated by water or methanol to a soft, semisolid material. |
| Polyphenylene Oxide | Insoluble in formic acid; meta cresol and other suitable solvents. |
| Polyphenylene Sulfide | Insoluble in formic acid and meta cresol at temperatures up to 100° C. |
| Polybenzimidazole | Insoluble in most suitable solvents; soluble in 50:50 dimethylformamide:dimethylsulfoxide; coagulates in cold water to give a weak, brown, opaque film which dries to a low-density opaque solid. |

*a Registered Trademark of DuPont de Nemours & Co. Inc.
**a Registered Trademark of General Electric Company

EXAMPLE 18

While the previous examples relate to the production of strong, transparent, homogeneous PLC materials in film form, the polymer solutions of my process can be formed into other desirable shapes without impediment to the process. Fibers of cellulose nitrate and cellulose triacetate containing 85% liquid have been prepared by vertical extrusion of 8% solutions in acetic and formic acid downward into a water bath at a temperature of 15° to 20° C. A Hercules RS-60 CN fiber containing 85% water showed an elongation at break of 47.5% and a shrinkage from a diameter of 16 mils to 5 mils during evaporative drying at constant length. When not constrained to prevent end-to-end shrinkage, a reduction in length of 40% was observed. 10mil cellulose triacetate fibers containing 85% water showed similar elongations at break, a 33% reduction in length during free drying, and a final diameter of 3.5 mils after drying at fixed length.

EXAMPLE 19

Another physical form of PLC materials with important commercial utility is a suspension of microspheres suitable for chromatographic application or as a vehicle for the controlled release of impregnants. Such microspheres can be prepared by emulsification of a suitable polymer solution in an immiscible liquid, followed by coagulation through mixing with a third liquid which is: (1) a nonsolvent for the polymer; (2) miscible with the solvent employed; and (3) also miscible with the emulsifying medium. Spherical microspheres with diameter of about 50 to 150 microns can be obtained. Microspheres of my PLC materials may range, for example, from about 5 to 300 microns, with a controlled internal pore size of from 10 to 200 Angstroms. Microspheres of my PLC materials having liquid contents as high as 98% are capable of absorbing, entrapping and releasing chemical compounds. Liquids are entrapped in the PLC structure by surface tension forces. The rate of diffusion of a chemical solute from the fine sponge-like structure of the material is approximately independent of time as the solvent slowly evaporates, so that the chemical will be released to its surroundings in about the same quantities as when the PLC microspheres are fully liquid and as when the liquid contents are almost entirely depleted. A solute with a pore size close to the pore size of the PLC material may be absorbed within the PLC material, and then entrapped therein by the partial drying of the PLC. My PLC material may vary in surface polarity, and in some cases, is not wetted by the very liquid which constitutes the liquid phase.

EXAMPLE 20

When the material is used as a semipermeable membrane, the molecular weight cutoff of the permeate fraction is a method of defining the pore size of the membrane and the material. The diffusive permeability is a method of determining the openness or permeability of the pores without the use of pressure as a driving force. For example, the molecular weight cutoff of a cellulose triacetate PLC material with 70% water is about 1500 to 5000 molecular weight (vitamin B-12 molecular weight 1355 retention 70%), and a retention of greater than 90% of cytochrome C with a molecular weight of 12,400. This indicates a pore diameter of about 14 Angstroms, while cellulose triacetate or cellulose nitrate with 85% water retains 10% of inulin with a molecular weight of 5200 and 87% of cytochrome C and 97% of hemoglobin with a molecular weight of 64,000, indicating a pore size of 25 Angstroms.

Cellulose triacetate with 92% water retains 7% of cytochrome C, 25% of bovine albumin (molecular weight 67,000), and greater than 98% of gamma globulin (molecular weight 153,000), indicating a pore size of 60 Angstroms. Cellulose triacetate with 97% water, 0% retention of gamma globulin, 42% retention of apoferritin (Molecular weight 480,000) and 93% retention of blue dextran 2000 (molecular weight about 2,000,000) indicate a pore diameter somewhat in excess of 200 Angstroms. Thus, my PLC material may have pore sizes of from about 10 to 250 Angstroms. My material acts as a membrane without the requirement of evaporation of solvent to form a Loeb-type layer thereon.

EXAMPLE 21

The presence of an electronegative, hydrogen-bond-accepting group not adjacent to the substituent-oxygen-cellulose bond is not in itself sufficient to allow formation of good polymer-liquid composites according to the process of Examples 1, 6 or 7, as shown by tests on cyanoethylcellulose having a degree of substitution of about 2.5. The polymer dissolves readily in formic acid, and is coagulated by water or isopropyl alcohol to a weak, white product which dries to an opaque white material devoid of physical strength.

EXAMPLE 22

A high degree of substitution does not allow successful PLC-formation from electropositively substituted cellulose derivatives, as shown by tests on tris(trimethylsilyl)cellulose of degree of substitution 3.00 prepared by reaction of cellulose with trimethyl silane under anhydrous conditions. Neither formic acid, acetic acid, nor meta cresol dissolves this fully substituted polymer, but a 6% solution in trifluoroacetic acid can be prepared. Trifluoroacetic acid serves as an excellent PLC-forming solvent for cellulose triacetate. Coagulation of this solution with water, methanol or isopropanol produces a white, waxy material which crumbles on handling and dries to an opaque, horny mass.

What I claim is:

1. A process of preparing a polymer-liquid composite material, which process comprises:
   a. providing a solvent solution of a cellulosic polymer having electronegative substituents, wherein the cellulosic polymer is selected from the group consisting of cellulose nitrate with a degree of substitution greater than about 2.25, cellulose acetate with a degree of substitution greater than about 2.90, a mixed cellulose nitrate and acetate cellulosic ester with a degree of substitution between about 2.25 and 2.90, and cellulose propionate with a degree of substitution greater than about 2.90, the solvent comprising a hydrogen-bonding solvent;

b. casting a wet film of the solvent solution;

c. forming an insoluble film by precipitating the cellulosic polymer in the wet film by contacting the film with a nonsolvent for the polymer, which nonsolvent is miscible with the solvent for the polymer so as to replace the solvent with the nonsolvent at a temperature below about 45° C to provide an essentially transparent, self-supporting, irreversibly shrinkable, ultramicroporous cellulosic polymer film having distinct interpenetrating cellulosic polymer and liquid nonsolvent phases.

2. The process of claim 1 wherein the solution comprises from about 0.5 to 15% by weight of the cellulosic polymer.

3. The process of claim 1 wherein the nonsolvent liquid phase comprises from about 70 to 98% of the composite material.

4. The process of claim 8 wherein the nonsolvent is water and the solvent is a hydroxyl or carboxyl-containing organic liquid.

5. The process of claim 1 wherein the nonsolvent is an organic liquid alcohol, and the solvent is a hydroxyl or carboxyl-containing organic liquid.

6. The process of claim 1 wherein the solvent is selected from the group consisting of acetic acid, methanol, diethyl ether, acetone and formic acid, and combinations of acetic acid and methanol with isopropanol and methylene chloride.

7. The process of claim 1 wherein the nonsolvent is selected from the group consisting of water, an alcohol, a hydrocarbon, an ester, an essential oil and combinations thereof.

8. The process of claim 1 which includes precipitating the cellulosic solvent solution so as to provide pore sizes of the cellulosic-liquid composite of from 10 to 200 Angstroms.

9. The process of claim 1 which includes the step of exchanging the first nonsolvent with another second nonsolvent, which second nonsolvent is miscible in the first nonsolvent.

10. The process of claim 9 which includes exchanging the nonsolvent by immersing the material in a solution of the second nonsolvent.

11. The process of claim 1 which includes evaporating all or a portion of the nonsolvent to provide for irreversible shrinkage of the film material.

12. The process of claim 1 which includes the step of sequentially exchanging the nonsolvent with another nonsolvent in which the first nonsolvent is miscible until a polymer-liquid material of the original polymer phase and the desired nonsolvent phase is obtained.

13. The process of claim 12 wherein the nonsolvent liquid in the exchange sequence comprises water-alcohol-hydrocarbon.

14. The process of claim 12 wherein the nonsolvent liquid in the exchange sequence comprises water-alcohol-essential oil.

15. A process for preparing a cellulosic-liquid composite material, which process comprises:

a. providing a solvent solution of cellulose polymer containing from about 0.5 to 15% cellulose polymer in a nondegrading hydrogen-bonding solvent, the cellulose polymer selected from the group consisting of cellulose nitrate with a degree of substitution greater than about 2.25, cellulose acetate with a degree of substitution greater than about 2.90, a mixed cellulose nitrate and acetate cellulosic ester with a degree of substitution between about 2.25 and 2.90, and cellulose propionate with a degree of substitution greater than about 2.90;

b. coating the cellulose polymer solution into a wet-film form; and c. precipitating the cellulose polymer in the wet film by immersing in a nonaqueous nonsolvent for the cellulose polymer, which nonsolvent is miscible with the solvent for the cellulose polymer, so as to replace the solvent with the nonsolvent by such immersion, the precipitation carried out at a temperature below about 40° C to provide a cellulose polymer-liquid composite film material having at least about 70% of the nonsolvent, the material essentially transparent, self-supporting, irreversibly shrinkable, ultramicroporous, with distinct interpenetrating cellulose nitrate and a liquid nonsolvent phase.

* * * * *